United States Patent [19]

Neiss et al.

[11] Patent Number: 4,661,515
[45] Date of Patent: Apr. 28, 1987

[54] COMPOUNDS HAVING ANGIOTENSIN CONVERTING ENZYME INHIBITORY ACTIVITY AND DIURETIC ACTIVITY

[75] Inventors: Edward S. Neiss, New Caanan; John T. Suh, Greenwich, both of Conn.; John J. Piwinski, Port Chester, N.Y.

[73] Assignee: USV Pharmaceutical Corporation, Tuckahoe, N.Y.

[21] Appl. No.: 821,201

[22] Filed: Jan. 17, 1986

Related U.S. Application Data

[63] Continuation of Ser. No. 589,031, Mar. 2, 1984, abandoned, which is a continuation of Ser. No. 400,555, Jul. 21, 1982, abandoned.

[51] Int. Cl.$^4$ .................. A61K 31/265; A61K 31/34; C07C 153/017; C07D 307/54
[52] U.S. Cl. ...................................... 514/471; 514/2; 514/512; 514/533; 514/570; 514/571; 514/595; 514/603; 514/620; 260/402 S; 260/404; 548/533; 549/492; 549/494; 558/240; 558/243; 558/248; 558/254; 558/276; 558/415; 560/12; 560/13; 560/16; 560/17; 560/22; 560/29; 560/30; 560/33; 560/34; 560/38; 560/39; 560/43; 562/426; 562/429; 562/430; 562/431; 562/437; 562/439; 562/443; 562/444; 562/449; 562/450; 562/452; 564/47; 564/48; 564/49; 564/50; 564/52; 564/155; 564/157; 564/158
[58] Field of Search .................... 260/112.5 R, 402.5, 260/404, 455 R, 455 B, 463, 465 D; 548/533; 549/492, 494; 560/12, 13, 16, 17, 22, 29, 30, 33, 34, 38, 39, 43; 562/426, 429, 430, 431, 437, 439, 443, 444, 449, 450, 452; 564/47, 48, 49, 50, 52, 155, 157, 158; 514/2, 471, 512, 533, 570, 571, 603, 595, 620

[56] References Cited

U.S. PATENT DOCUMENTS

| | | | |
|---|---|---|---|
| 4,046,889 | 9/1977 | Ondetti et al. | 424/274 X |
| 4,053,651 | 10/1977 | Ondetti et al. | 424/319 |
| 4,256,761 | 3/1981 | Suh et al. | 424/282 |
| 4,374,829 | 2/1983 | Harris et al. | 424/177 |
| 4,431,644 | 2/1984 | Smith et al. | 424/246 |
| 4,431,645 | 2/1984 | Smith et al. | 424/246 |
| 4,450,275 | 5/1984 | Arimura et al. | 548/201 |
| 4,482,725 | 11/1984 | Ondetti et al. | 548/533 |
| 4,483,861 | 11/1984 | Iwao et al. | 424/263 |
| 4,496,578 | 1/1985 | Iwao et al. | 548/533 |

FOREIGN PATENT DOCUMENTS 889152 12/1981 Belgium .
WO80/00700 4/1980 Japan .
2045249 10/1980 United Kingdom .

OTHER PUBLICATIONS

Ondetti et al., Chemical Abstracts, vol. 96 (1982) 1433246 of French Patent 2,479,827 (10-9-81).
Iwao et al., Chemical Abstracts, vol. 93 (1980) 204627g of Ger. Offen. 2,944,037 (5-8-80).
Arimura et al., Derwent of Belgium Pat. No. 879,158 (2-1-80).

Primary Examiner—Richard L. Raymond

[57] ABSTRACT

Novel compounds possessing both angiotensin enzyme inhibitory activity and diuretic activity are disclosed. The compounds are represented by the general formula

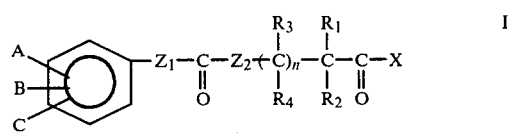

in which X is

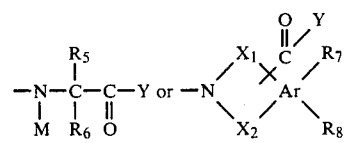

in which $R_1$, $R_2$, $R_3$, $R_4$, $R_5$ and $R_6$ are hydrogen, alkyl, alkenyl, alkynyl, phenyl-alkyl, and cycloalkyl, and may be the same or different; n is an integer from 0 to 4 inclusive; M is alkenyl, alkynyl, cycloalkyl, cycloalkyl-alkyl, polycycloalkyl, polycycloalkyl-alkyl, aryl, aralkyl, heteroaryl, heteroaryl-alkyl, hetero-cyloalkyl, hetero-cycloalkyl-alkyl, fused aryl-cycloalkyl, fused aryl-cycloalkyl-alkyl, fused heteroaryl-cycloalkyl, fused heteroaryl-cycloalkyl-alkyl, alkoxyalkyl, alkylthioalkyl, alkylamino-alkyl, or dialkylaminoalkyl, or M and $R_6$ taken together with the nitrogen to which M is bonded and the carbon to which $R_6$ is bonded form a saturated unsubstituted heterocyclic group containing 3 or 4 ring carbon atoms; Y is hydroxy, alkoxy, amino, or substituted amino, aminoalkanoyl, aryloxy, aminoalkoxy, or hydroxyalkoxy; $Z_1$ and $Z_2$ each is a chemical bond, the group $X_3$—$(CH_2)_m$, an amino acid group or the group $X_3$—$(CH_2)_m$—$X_3$ wherein $X_3$ is oxygen, sulfur or NH and m is an integer from 0 to 4 inclusive; A and B each is the same as $R_1$ or halogen, trifluoromethyl, $OR_1$, $NO_2$, $NR_1R_2$, $SO_2NH_2$, CN, $SR_1$, $SOR_1$, $SO_2R_1$, $CONR_1R_2$, $COOR_1$; C is hydrogen alkyl, heteroallyl, amino, —$CR_1$=$CR_2$—,

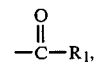

aminoalkyl, furfurylmethylamino, aminoaryl or aminobenzyl; $X_1$ and $X_2$ are each S, SO, $SO_2$, $NR_1$, O, chemical bond, $(CR_9R_{10})_m$, —$CR_9$=$CR_{10}$—, and CHOH, with the proviso that at least one of $X_1$ and $X_2$ be $(CR_9R_{10})_m$, wherein $R_9$ and $R_{10}$ are each hydrogen or lower alkyl, and m is an integer from 1 to 5; Ar is a divalent arylene or heteroarylene; and $R_7$ and $R_8$ are each hydrogen, alkyl, halo, cyano, hydroxy, alkoxy, amino, alkylamino, dialkylamino, mercapto, alkylmercapto, nitro, trifluoromethyl, carboxy, carbalkoxy, COY and $NHCONHR_1$ wherein $R_1$ and Y are as hereindefined; and pharmaceutically-acceptable salts thereof.

18 Claims, No Drawings

COMPOUNDS HAVING ANGIOTENSIN CONVERTING ENZYME INHIBITORY ACTIVITY AND DIURETIC ACTIVITY

This application is a continuation of our prior application Ser. No. 589,031, filed Mar. 2, 1984, now abandoned, which was a continuation of our previous copending application Ser. No. 400,555, filed July 21, 1982, now abandoned.

BACKGROUND OF THE INVENTION

This invention relates to new chemical compounds combining angiotensin converting enzyme inhibitory activity and diuretic activity.

Compounds are known which are capable of suppressing or inhibiting the conversion of angiotensin I to angiotensin II, a property making them useful in the treatment of hypertension. Illustrative of such compounds are those disclosed in U.S. Pat. No. 4,105,776 and having the general formula

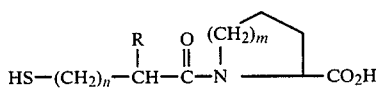

in which R is hydrogen or alkyl of 1 to 7 carbon atoms, preferably methyl, m is 1 or 2 and n is 0 or 1, and those disclosed in U.S. Pat. No. 4,256,761 and having the general formula

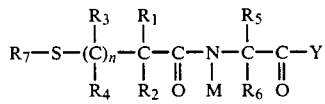

in which $R_1$, $R_2$, $R_3$, $R_4$, $R_5$, and $R_6$ are hydrogen, alkyl, alkenyl, alkynyl, phenyl-alkyl, and cycloalkyl, and may be the same or different; n is an integer from 0 to 4 inclusive; M is alkenyl, alkynyl, cycloalkyl, cycloalkylalkyl, polycycloalkyl, polycycloalkyl-alkyl, aryl, aralkyl, heteroaryl, heteroaryl-alkyl, hetero-cycloalkyl, hetero-cycloalkyl-alkyl, fused aryl-cycloalkyl, fused aryl-cycloalkyl-alkyl, fused heteroaryl-cycloalkyl, fused heteroaryl-cycloalkyl-alkyl, alkoxyalkyl, alkylthioalkyl, alkylamino-alkyl, or dialkylamminoalkyl; Y is hydroxy, alkoxy, amino, or substituted amino, aminoalkanoyl, aryloxy, aminoalkoxy, or hydroxyalkoxy; and, $R_7$ is hydrogen, alkanoyl, carboxyalkanoyl, hydroxyalkanoyl, aminoalkanoyl, cyano, amidino, carbalkoxy, ZS, or

wherein Z is hydrogen, alkyl, hydroxyalkyl, or the radical

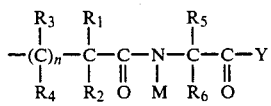

wherein $R_1$, $R_2$, $R_3$, $R_4$, $R_5$, $R_6$, n, M and Y are as described above; and where Y is hydroxy, pharmaceutically acceptable alkali metal, alkaline earth metal, and amine salts.

In addition, in commonly assigned U.S. patent application Ser. No. 148,083, filed May 12, 1980 are described compounds having angiotension converting enzyme inhibitory activity of the following structure:

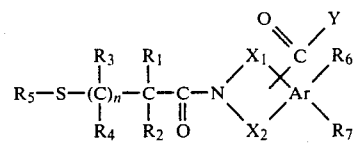

wherein:
$R_1$, $R_2$, $R_3$ and $R_4$ are each hydrogen, alkyl, alkenyl, alkynyl, aryl, heteroaryl, aralkyl, heteroaralkyl, cycloalkyl, polycycloalkyl, or heterocycloalkyl;
n is an integer from 0 to 4 inclusive;
$R_5$ is hydrogen, alkyl, aralkyl, aryl, hydroxyalkyl, aminoalkyl, alkanoyl, aryloyl, arylalkanoyl, hydroxyalkanoyl, carboxyalkanoyl, aminoalkanoyl, cyano, amino, alkylamino, arylamino, amidino, alkylamidino, arylamidino, or ZS—, $ZS(CR_1R_2)_n$— or ZSCO— wherein Z is alkyl, aryl, aralkyl or a radical of the formula

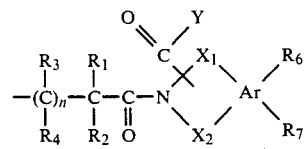

wherein $R_1$, $R_2$, $R_3$, $R_4$, $R_6$, $R_7$, n, $X_1$, $X_2$ and Y are as herein defined;
Y is OH, OM, $OR_1$, $NR_1R_2$, $-NR_1-(CR_1R_2)_n-CO-Y^1$ wherein M is a pharmaceutically acceptable cation, $R_1$, $R_2$ and n are as herein defined, and $Y_1$ is OH, OM, $OR_1$ or $NR_1R_2$;
$X_1$ and $X_2$ are each S, SO, $-SO_2$, $NR_1$, chemical bond, O, $(CR_8R_9)_m$, $-CR_8=CR_9-$, and CHOH, with the proviso that at least one of $X_1$ and $X_2$ be $(CR_8R_9)_m$, wherein $R_8$ and $R_9$ are each hydrogen or lower alkyl, and m is an integer from 0 to 5;
Ar is a divalent arylene or heteroarylene; and
$R_6$ and $R_7$ are each hydrogen, alkyl, halo, cyano, hydroxy, alkoxy, amino, alkylamino, dialkylamino, mercapto, alkylmercapto, nitro, trifluoromethyl, carboxy, carbalkoxy, COY, and $NHCONHR_1$, wherein $R_1$ and Y are as herein defined.

Numerous diuretics are known in the art including the benzene sulfonamides described in U.S. Pat. No. 3,058,882 and having the general formula

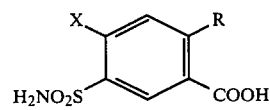

in which X represents a chlorine or bromine atom and R represents a benzylamino, dibenzylamino, furfurylamino or thenylamino group, and the salts thereof, and the (α-alkylidene acyl)phenoxy and (α-alkylidene acyl) phenyl-mcrcapto derivatives of monocarboxylic acids described in U.S. Pat. No. 3,255,241 and having the general formula

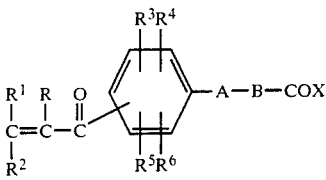

in which R, $R^1$ and $R^2$, respectively, is selected from the group consisting of hydrogen; halogen or halogen-like radicals; hydroxyl; lower aliphatic, lower aliphatic-oxy or lower aliphatic-thio, straight or branched chain, saturated or unsaturated, and unsubstituted or substituted, the substituent group(s) being alkyl, amino, halogen-like, carboxyl or substituted carboxyl, cyano, hydroxyl, alkylthio, arylthio, arylsulfonyl, alkylsulfonyl, nitro, and the like; alicyclic, either unsubstituted or substituted, the substituent groups being the same as those described above for the aliphatic group; aryl or aryloxy or aryl-thio, especially phenyl, phenoxy or phenylthio, wherein the aryl-(phenyl) moiety can be unsubstituted or a substituent can be attached to one or more of its carbon atoms selected advantageously from lower, straight or branched chain-alkyl, alkoxy, alkylthio, hydroxyl, halogen, halogen or halogen-like; arylaliphatic, especially a mononuclear-arylaliphatic, advantageously phenalkyl which can be attached through an oxygen or a sulfur atom to the grouping

and which is either unsubstituted or substituted in the aryl and/or alkyl portions by substituents of the aforesaid type; cyano; and wherein R and $R^2$ additionally can be linked together to form preferably a 5 to 6 carbon ring with the carbons to which they are attached; $R^3$, $R^4$, $R^5$ and $R^6$ respectively can represent the same or different group selected from hydrogen, halogen, lower aliphatic, straight or branched chain; lower aliphatic-oxy or lower aliphatic-thio, straight or branched chain; unsubstituted or having a substituent of the type described above for attachment to the lower aliphatic group; and wherein the lower aliphatic-oxy or lower aliphatic-thio is advantageously lower alkoxy or loweralkylthio, unsubstituted or substituted, as for example, carboxyalkoxy, carboxyalkylthio, and the like; aliphaticsulfonyl, especially an alkylsulfonyl; hydroxyl; nitro; amino-carboxy or substituted carboxy, especially carbamoyl and N-substituted carbamoyl; aryl, especially phenyl unsubstituted or substituted as described above for attachment to aryl (phenyl) moieties; or wherein $R^3$ and $R^4$ and/or $R^5$ and $R^6$ can additionally be linked together to form, with the ring carbons to which they are attached, a 5- or 6- membered carbocyclic ring; A represents oxygen or sulfur which can be oxidized to the sulfoxide or sulfone; B represents a divalent aliphatic, aromatic or aliphatic-aromatic group, preferably a straight or branched chain lower aliphatic group which can contain oxygen or sulfur atoms as part of the aliphatic chain; a phenyl-lower alkyl, or a phenyl group; X represents hydroxyl or salts of the resulting acids, i.e., metal salts, especially sodium, potassium, calcium and the like or amino salts; alkoxy, unsubstituted or substituted, the substituent(s) being dialipnatic amino and the like; amino such as an amino group of the structure —$NR^7R^6$ wherein $R^7$ and $R^6$ are the same or different; aliphatic, unsubstituted or substituted, group or aromatic, unsubstituted or substituted, group, especially substituted phenyl or $R^7$ and $R^6$ can be joined together to form, with the nitrogen atom to which they are attached, a hetero ring containing one or more hetero atoms as morpholinyl, piperazinyl, pyrrolidyl and the like; and, hydrazine, unsubstituted or substituted, advantageously with lower-alkyl group or groups.

The disclosures of U.S. Pat. Nos. 3,058,882, 3,255,241, 4,105,776 and 4,256,761 are incorporated by reference herein.

SUMMARY OF THE INVENTION

Unlike the compounds of the prior art, supra, which possess either angiotensin converting enzyme inhibitory activity or diuretic activity, the compounds of the present invention combine borh activities in a single molecular species. The compounds of this invention are represented by the general formula

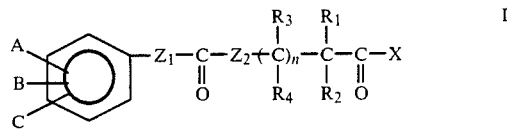

in which X is

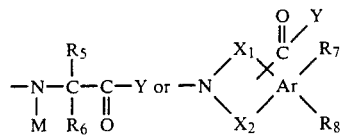

in which $R_1$, $R_2$, $R_3$, $R_4$, $R_5$ and $R_6$ are hydrogen, alkyl, alkenyl, alkynyl, phenyl-alkyl, and cycloalkyl, and may be the same or different; n is an integer from 0 to 4 inclusive; M is alkenyl, alkynyl, cycloalkyl, cycloalkyl-alkyl, polycycloalkyl, polycycloalkyl-alkyl, aryl, aralkyl, hereroaryl, heteroaryl-alkyl, hetero-cycloalkyl, hetero-cycloalkyl-alkyl, fused aryl-cycloalkyl, fused aryl-cycloalkyl-alkyl, fused heteroaryl-cycloalkyl, fused heteroaryl-cycloalkyl-alkyl, alkoxyalkyl, alkylthioalkyl, alkylamino-alkyl, or dialkylaminoalkyl, or M and $R_6$ taken together with the nitrogen to which M is bonded and the carbon to which $R_6$ is bonded form a saturated unsubstituted heterocyclic group containing 3 or 4 ring carbon atoms; Y is hydroxy, alkoxy, amino, or substituted amino, aminoalkanoyl, aryloxy, aminoalkoxy, or hydroxyalkoxy; $Z_1$ and $Z_2$ each is a chemical bond, the group $X_3$—$(CH_2)_m$, an amino acid group or the group $X_3$—$(CH_2)_m$—$X_3$ wherein $X_3$ is oxygen, sulfur or NH and m is an integer from 0 to 4 inclusive; A and B each is the same as $R_1$ or halogen, trifluoromethyl, $OR_1$, $NO_2$, $NR_1R_2$, $SO_2NH_2$, CN, $SR_1$, $SOR_1$, $SO_2R_1$, $CONR_1R_2$, $COOR_1$; C is hydrogen alkyl, heteroallyl, amino, —$CR_1$=$CR_2$—,

aminoalkyl, furfurylmethylamino, methylamino aminoaryl or aminobenzyl; $X_1$ and $X_2$ are each S, SO, $SO_2$, $NR_1$, O, chemical bond, $(CR_9R_{10})_m$, —$CR_9$=CR- 10—, and CHOH, with the proviso that at least one of $X_1$ and $X_2$ be $(CR_9R_{10})_m$, wherein $R_9$ and $R_{10}$ are each hydrogen or lower alkyl, and m is an integer from 1 to 5; Ar is a divalent arylene or heteroarylene; and $R_7$ and $R_8$ are each hydrogen, alkyl, halo, cyano, hydroxy, alkoxy, amino, alkylamino, dialkylamino, mercapto, alkylmercapto, nitro, trifluoromethyl, carboxy, carbalkoxy, COY and $NHCONHR_1$ wherein $R_1$ and Y are as hereindefined; and pharmaceutically-acceptable salts thereof.

DESCRIPTION OF THE PREFERRED EMBODIMENTS

Preferred compounds of the present invention are those of the above general formula in which $R_1$, $R_2$, $R_3$ and $R_4$ each is hydrogen or a lower alkyl group, preferably methyl; n is 1; M is cycloalkyl; one of $X_1$ and $X_2$ is $-CH_2-$ and the other is $-CH_2-CHR_1-$, Ar is o-phenylene; Y is hydroxy or alkoxy; $Z_1$ is carbonyl, chemical bond, or the group $-OCH_2-$; $Z_2$ is sulfur; A and B each is hydrogen, halogen or the group $-SO_2NH_2$; and C is halogen, amino,

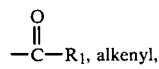
$-C-R_1$, alkenyl, aminoalkyl, furanylmethylamino, aminoaryl or aminobenzyl.

The alkyl groups per se and in the alkyl moiety in aralkyl, cycloalkylalkyl, polycycloalkylalkyl, heteroarylalkyl and the like, and, in alkoxy, alkylmercapto, alkanoyl, carbalkoxy, alkylamino and dialkylamino, may be straight chained or branched and are preferably alkyl groups containing from 1 to 20 carbons. Such groups include methyl, ethyl, propyl, isopropyl, butyl, isobutyl, amyl, iso-amyl, hexyl, octyl, dodecyl, and the like. Preferably the alkyl groups are lower alkyl containing from 1 to 6 carbon atoms.

The alkenyl and alkynyl groups may also be branched or straight chained and contain from 2 to 6 carbon atoms. Such groups include vinyl, ethynyl, propenyl, allyl, isopropenyl, and the like.

Thase alkyl, alkenyl, and alkynyl groups may carry substituents such as hydroxy, alkoxy, amino, alkylamino, dialkylamino, mercapto, alkylmercapto, halo, and the like.

The cycloalkyl, polycycloalkyl, aryl, heteroaryl, aryalkyl, fused aryl-cycloalkyl, groups and the like contain from 3 to 16 carbon atoms and may carry substituents such as lower alkyl, alkenyl, alkynyl, hydroxy, mercapto, amino, alkoxy, alkylmercapto, alkylamino, dialkylamino, halo, trifluoromethyl and the like. The groups include such radicals as cyclopropyl, cyclobutyl, cyclopentyl, cyclohexyl, cycloheptyl, adamantyl, norbornyl, phenyl, tolyl, benzyl, penethyl, dimethoxyphenyl, hydroxybenzyl, indanyl, naphthyl, tetrahydronaphthyl, decanhydronaphthyl, pyridyl, quinolyl, pyrrolidyl, pyrrolyl, morpholinyl, furyl, furfuryl, tetrahydrofurfuryl, benzimidazolyl, thienyl, imidazolyl, and the like.

The halo groups include fluoro, chloro, bromo and iodo.

Compounds in accordance with the present invention are readily prepared employing known starting materials and procedures. It will be understood by those skilled in the art that compounds having an asymmetric carbon may exist in both levo and dextro forms, said forms being within the scope of the invention.

The present new compounds can be prepared by reaction of an acylating derivative of an acid of the formula

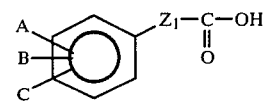

with a compound of the formula

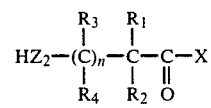

in which substituents. A, B, C, Z, $Z_2$, $R_1$, $R_2$, $R_3$, $R_4$, n and X are as defined hereinbefore.

The acylating derivative can be the free acid, acyl halide, lower alkyl ester, anhydride, and mixed anhydride, e.g., with acetic acid. The acylation reaction is conveniently effected using the free carboxylic acid, preferably with carbodiimides present as are commonly used in peptide synthesis, e.g., N,N-dicyclohexylcarbodiimide. A reaction solvent is normally used to permit more intimate contact of the reactants and includes such solvents as ethers of ethylene glycol and diethylene glycol, tetrahydrofuran, dioxane, alkyl ketones such as acetone, methyl isobutyl ketone and similar solvents. Reaction temperature is not critical since the reaction proceeds smoothly at room temperature and even at lower temperatures. The use of high temperature for the reaction, e.g., reflux temperature of the reaction mixture, will shorten the reaction time but may lead to undesirable by-products. Generally, the reaction is allowed to proceed at room temperature until complete. The products are recovered by usual methods and purified as by recrystallization from suitable solvents.

In those compounds where free acid groups are present, e.g., where Y is OH, the compounds can readily form salts with suitable cations, preferably those which are pharmaceutically acceptable, e.g., both mono and polyvalent metal ions such as sodium, potassium, calcium, magnesium, iron and the like, and ammonium ions derived from ammonia, primary secondary and tertiary amines.

The following examples are illustrative of the present invention.

EXAMPLE I

This example illustrates the preparation of intermediates used in the preparation of compounds of this invention.

A. N-Cyclopentylglycine t-butyl ester

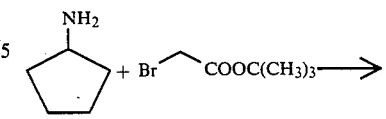

-continued

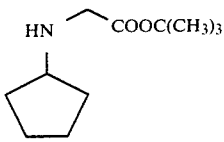

To a solution containing 75 g (0.88 mol) of cyclopentylamine and 100 g (1.0 mol) of triethylamine in 500 ml of ether at 0° C. was slowly added 136 g (0.70 mol) of t-butyl bromoacetate in 200 ml of ether. After stirring at room temperature for 6 hours, the mixture was filtered, washed with water, and concentrated in vacuo. The residue was acidified with 5% aqueous HCl, washed with ether, rendered basic with 5% aqueous $K_2CO_3$, and extracted with ether. The ethereal solution was then washed with water, dried over $MgSO_4$, and concentrated in vacuo to give 90 g (65%) of N-cyclopentylglycine, t-butyl ester as an oil which crystallized on standing.

B.
N-(3-Acetylthio-2-methylpropanoyl)-N-cyclopentylglycine t-butyl ester

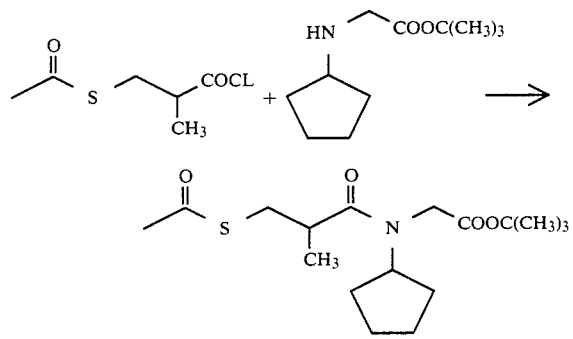

To a solution containing 60 g (0.30 mol) of N-cyclopentylglycine t- butyl ester and 75 ml (0.54 mol) of triethylamine in 200 ml of methylene chloride at 0° C. was added dropwise a solution of 54 g (0.30 mol) of 3-acetylthio-2-methylpropanoyl chloride in 250 ml of methylene chloride. After the reaction mixture was stirred at room temperature overnight, it was filtered and concentrated in vacuo. The residue was taken up in ethyl acetate and wasned once with saturated aqueous $NaHCO_3$, once with brine, three times with 5% aqueous HCl, once with brine, and five times with saturated aqueous $NaHCO_3$. The organic phase was dried over $MgSO_4$, filtered, and concentrated in vacuo to yield 80.1 g (78%) of N-(3-acetylthio-2-methylpropanoyl)-N-cyclopentylglycine t-butyl ester as an oil which crystallized on standing.

C. N-(3-Acetylthio-2-methylpropanoyl)-N-cyclopentyl glycine

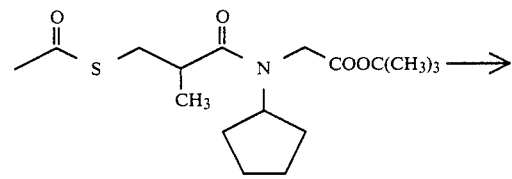

-continued

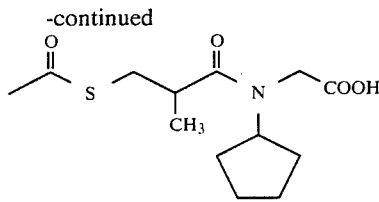

A mixture containing 80.1 g (0.23 mol) of N-(3-acetylthio-2-methyl-propanoyl)-N-cyclopentyl glycine t-butyl ester, 37.9 g (0.35 mol) of trimethysilyl chloride, and 52.5 g (0.35 mol) of sodium iodide in 300 ml of acetonitrile was heated between 45°-50° C. for 30 minutes. Following the addition of 50 ml of water, the mixture was concentrated in vacuo. The residue was rendered basic with 400 ml of saturated aqueous $NaHCO_3$, washed three times with ethyl acetate, acidified with concentrated HCl, and extracted three times with ethyl acetate. These later organic extracts were combined, dried over $MgSO_4$, filtered, and concentrated in vacuo to afford 60 g (91%) of the crude product. Purification via high pressure liquid chromatography (HPLC) [ethyl acetate/hexane/acetic acid (60/40/2)] afforded N-(3-acetylthio-2-methylpropanoyl)-N-cyclopentyl glycine as an oil.

D. N-(3-Mercapto-2-methylpropanoyl)-N-cyclopentyl glycine

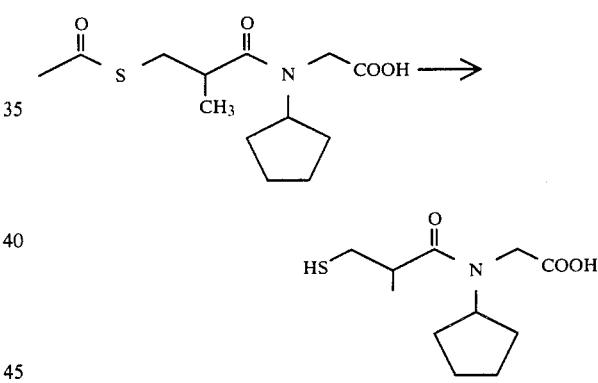

Into a solution containing 10.4 g (36 mmol) of N-(3-acetylthio-2- methylpropanoyl)-N-cyclopentyl glycine was bubbled ammonia gas for 1 hour. After 20 minutes the mixture was concentrated in vacuo, and the residue taken up in ethyl acetate and washed three times with 5% aqueous sodium bisulfate. It was then dried over $MgSO_4$, filtered, concentrated in vacuo, and purified via HPLC [ethyl acetate toluene/hexane/acetic acid (50/25/50/2)] to give 7.9 g (90%) of N-(3-mercapto-2-methylpropanoyl)-N-cyclopentyl glycine as an oil.

E. N-(3-Mercapto-2-methylpropanoyl)-N-cyclopentyl glycine methyl ester

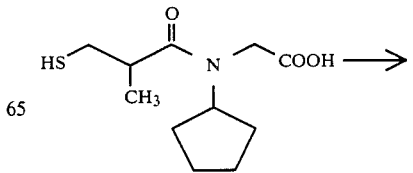

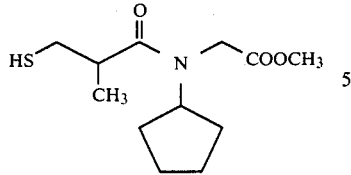

A mixture containing 19.0 g (77 mmol) of N-3-mercapto-2-methylpropanoyl)- N-cyclopentyl glycine and 2.0 g (10.5 mmol) of p-toluene sulfonic acid in 500 ml of methanol was refluxed overnight. The reaction mixture was concentrated in vacuo and the residue taken up in ether. It was washed once with saturated aqueous sodium bicarbonate and once with brine. The organic phase was dried over MgSO₄, filtered, and concentrated in vacuo to afford N-(3-mercapto-2-methylpropanoyl)-N-cyclopentyl glycine methyl ester as an oil.

F.
N-(3-Mercapto-2-methylpropanoyl)-N-cyclopentylglycine t-butyl ester

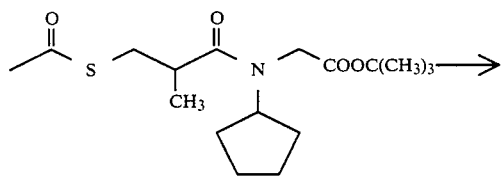

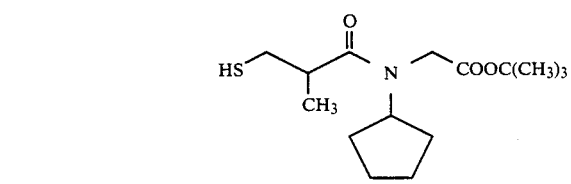

Into a solution containing 50 g (0.14 mol) of N-(3-acetylthio-2-methylpropanoyl)-N-cyclopentylglycine t-butyl ester in 700 ml of methanol was bubbled nitrogen gas for 10 minutes followed by ammonia gas for 30 minutes. After 30 minutes the mixture was concentrated in vacuo and the residue taken up in ethyl acetate. It was washed once with 3% aqueous HCl and once with water, dried over MgSO₄, filtered, and concentrated in vacuo to yield an oily product. Purification via HPLC [15% ethyl acetate in hexanes] afforded 30 g (70%) of N-(3-mercapto-2-methyl-propanoyl)-N-cyclopentylglycine t-butyl ester as an oil.

EXAMPLE 2

N-[3-[2,3-Dichloro-4-(2-methylene-1-oxobutyl) phenoxy]acetylthio-2-methylpropanoyl]-N-cyclopentyl glycine methyl ester

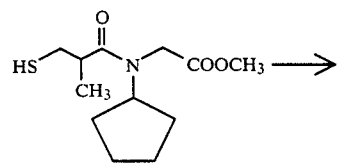

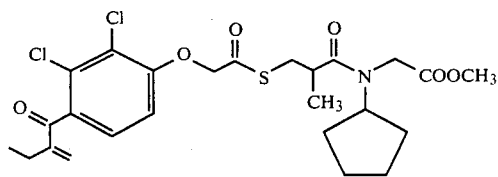

To a solution containing 10.5 g (40.0 mmol) of N-(3-mercapto-2-methylpropanoyl)-N-cyclopentyl glycine methyl ester and 12.1 g (39.9 mmol) of ethacrynic acid in 200 ml of glyme at 0° C. was added a solution of 8.24 g (39.9 mmol) of N,N-dicyclohexylcarbodiimide in 20 ml of glyme. The solution was allowed to warm to room temperature and to stir overnight. The mixture was filtered and the filtrate concentrated in vauco. Purification of the product by HPLC [hexane/ethyl acetate/acetone (70/20/15)] afforded N-[3-[2,3-dichloro-4-(2-methylene-1-oxobutyl) phenoxy]]acetylthio-2-methylpropanoyl]-N-cyclopentyl glycine methyl esrer as a viscous oil.

EXAMPLE 3

N-[3-[2,3-Dichloro-4-(2-methylene-1-oxobutyl)pnenoxy]acetylthio-2-methylpropanoyl]-N-cyclopentyl glycine t-butyl ester

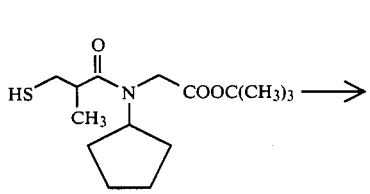

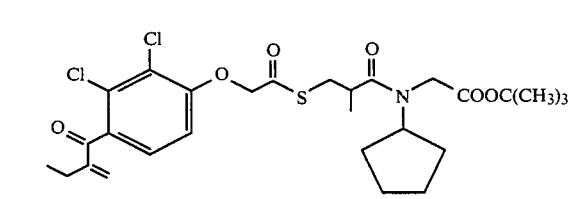

To a solution containing 19.2 g (63.8 mmol) of N-(3-mercapto-2-methylpropanoyl)-N-cyclopentylglycine t-butyl ester and 19.3 g (63.7 mmol) of ethacrynic acid in 20 ml of methylene chloride at 0° C. was added a solution of 13.2 g (64.0 mmol) of N,N-dicyclohexylcarbodiimide in 20 ml of methylene chloride. The solution was allowed to warm to room temperature and to stir overnight. The solution was filtered and the filtrate was concentrated in vacuo. Purification of the product by HPLC [10% ethyl acetate in hexanes] afforded N-[3-[2,3-dichloro-4-(2-methylene-1-oxobutyl) phenoxy] acetylthio-2-methylpropanoyl]-N-cyclopentyl glycine t-butyl ester as a viscous oil.

EXAMPLE 4

N-[3-[2,3-Dichloro-4-(2-methylene-1-oxobutyl)phexoxy]acetylthio-2-methylpropanoyl]-N-cyclopentyl glycine

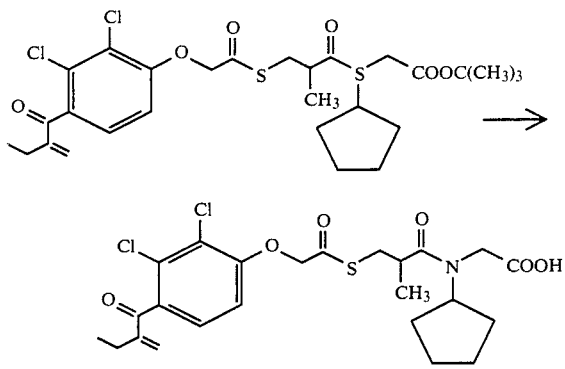

To a solution containing 5.2 g (8.7 mmol) of N-[3-[2,3-dichloro-4-(2-methylene-1-oxobutyl)phenoxy]acetylthio-2-methylpropanoyl]-N-cyclopentyl glycine t-butyl ester in 100 ml of methylene chloride was added 9.0 ml (117 mmol) of trifluoroacetic acid. After 12 hours the reaction mixture was carefully concentrated in vacuo and the residue was chromatographed via HPLC [methylene chloride/ether/acetic acid (88/10/2.5)]to' afford 2.4 g (52%) of N-[3-[2,3-dichloro-4-(2-methylene-1-oxobutyl) phenoxy] acetylthio-2methylpropanoyl]-N-cyclopentyl glycine as a glass.

EXAMPLE 5

N-[3-(4-chloro-2-[(2-furanylmethyl) amino]-5-sulfamoyl) benzoylthio-2-methylpropanoyl]-N-cyclopentyl glycine t-butyl ester

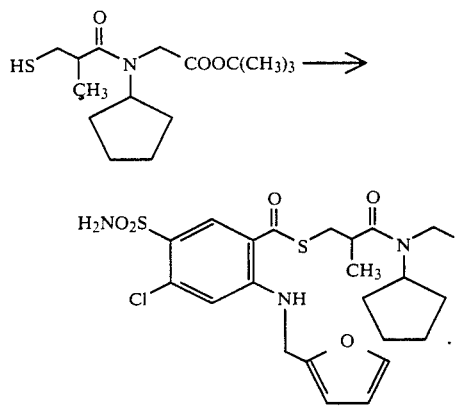

To a solution containing 11.5 g (38.2 mmol) of N-(3-mercapto-2-methylpropanoyl)-N-cyclopentylglycine t-butyl ester and 12.6 g (38.1 mmol) of furosemide in 100 ml of tetrahydrofuran and 35 ml of acetone at 0° C. was added 7.84 g (38.0 mmol) of N,N-dicyclohexylcarbodiimide in 20 ml of tetrahydrofuran. The solution was slowly allowed to warm to room temperature and to stir overnight. The solution was filtered and the filtrate was concentrated in vacuo. Purification of the product by HPLC [Hexane/ethyl acetate/acetone (4/1/1)]afforded N-[3-(4-chloro-2-[(2-furanylmethyl) amino]-5-sulfamoyl) benzoylthio-2-methylpropanoyl]-N-cyclopentyl glycine t-butyl ester as a glass.

EXAMPLE 6

N-[3-(4-chloro-2-[(2-furanylmethyl)amino]-5-sulfamoyl) benzoylthio-2-methylpropanoyl]-N-cyclopentyl glycine

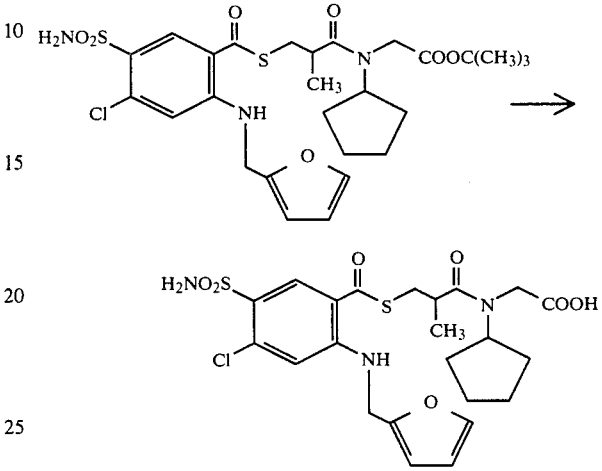

Into a solution containing 7.72 g (7.69 mmol) of N-[3-(4-chloro-2-[(2-furanylmethyl) amino]-5-sulfamoyl) benzoylthio-2-methylpropanoyl]-N-cyclopentyl glycine. t-butyl ester and 624 ul (7.72 mmol) of pyridine in 100 ml of methylene chloride at −10° C. was bubbled isobutylene for 5 minutes. To this solution was then added dropwise 2.03 ml (14.3 mmol) of trimethylsilyl iodide. After 2 hours the reaction was quenched by the addition of 1.0 ml of water. The solution was concentrated in vacuo and the residue was taken up in a chloroform/methylene chloride mixture. The precipitated solid was filtered off and recrystallized two times from an acetonitrile/ethanol/water mixture to afford 1.2 g (28%) of N-[3-(4-chloro-2-[(2-furanylmethyl) amino]-5-sulfamoyl) benzoylthio-2-methylpropanoyl]-N-cyclopentyl glycine as a yellow solid: M.P. 204°–206° C.

In the same manner the mercaptan compounds in Column A are acylated by the acids in Column B to provide the compounds in Column C after cleavage of their t-butyl esters.

| A<br>Mercaptan | B<br>Actylated Acid | C<br>Product |
|---|---|---|
| 1. N—(3-mercapto-2-methylpropanoyl)-N—cyclopentyl glycine t-butyl ester | bumetanide | N—[3-(5-butylamino-4-phenoxy-3-sulfamoyl) benzoylthio-2-methylpropanoyl]-N—cyclopentyl glycine. |
| 2. N—(3-mercapto-2-methylpropanoyl)-N—cyclopentyl glycine t-butyl ester | piretanide | N—[3-(4-phenoxy-5-pyrrolidinyl-3-sulfamoyl)benzoylthio-2-methylpropanoyl]-N—cyclopentyl glycine. |
| 3. N—(3-mercapto-2-methylpropanoyl)-N—cyclopentyl glycine t-butyl ester | xipamide | N—[3-(4-chloro-2-hydroxy-5-sulfanoyl)benzothio-2-methylpropanoyl]-N—cyclopentyl glycine. |
| 4. N—(3-mercapto-2-methylpropanoyl)-N—cyclopentyl glycine t-butyl ester | 4-benzoyl-3-sulfamoyl-5-(3-thienyl-methyloxy)-benzoic acid | N—[3-(4-benzoyl-3-sulfamoyl-5-(3-thienyl-methyloxy)]benzoylthio-2-methylpropanoyl]-N—cyclopentyl glycine. |
| 5. N—(3-mercapto-2- | tienilic acid | N—[3-[2,3-dichloro-4- |

| A<br>Mercaptan | B<br>Actylated Acid | C<br>Product |
|---|---|---|
| methylpropanoyl)-1,2,3,4-tetrahydroiso-quinoline-3-carboxylic acid t-butyl ester | | (2-thienylcarbonyl) phenoxy]acetylthio-2-methylpropanoyl]-N—cyclopentyl glycine. |
| 6. N—(3-mercapto-2-methylpropanoyl)-1,2,3,4-tetrahydroiso-quinoline-3-carboxylic acid t-butyl ester | 2-(2-furfuryl-amino)-4-phenoxy-5-sulfamoyl-benzoic acid | N—3-[2-(2-furfuryl-amino)-4-phenoxy-5-sulfamoyl]benzoylthio-2-methylpropanoyl]-N—cyclopentyl glycine. |

5-Sulfamyl-4-chloro-2-[(2'-furanylmethyl)amino]benzoic acid is reacted with mercaptan compound #1 to form the corresponding acylated mercaptan. Similarly, 5-sulfamyl-2-[(2'-furanylmethyl)amino]-4-phenoxybenzoic acid with mercaptan compound #2 and 2,3-dichloro-4-(2-methylene-1-oxobutyl)phenoxyacetic acid with compound #5 forms acylated mercaptans.

What is claimed is:

1. A compound of the formula

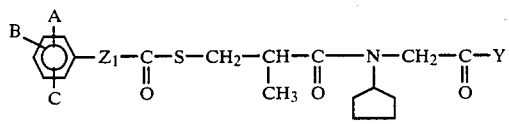

and pharmaceutically acceptable salts thereof; wherein
$Z_1$ is a chemical bond or —OCH$_2$—,
A and B are independently hydrogen, halogen or —SO$_2$NH$_2$,
C is hydrogen,

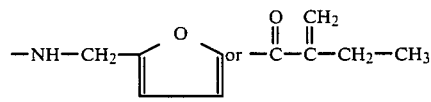

with the proviso that at least one of A, B, or C is other than hydrogen, and
Y is hydroxy or lower alkoxy.

2. The compound which is N-[3-[2,3-Dichloro-4-(2-methylene -1-oxobutyl) phenoxy] acetylthio-2-methylpropanoyl]-N-cyclopentyl glycine methyl ester.

3. The compound which is N-[3-[2,3-Dichloro-4-(2-methylene-1-oxobutyl)phenoxy] acetylthio-2-methyl-panoyl]-N-cyclopentyl glycine t-butyl ester.

4. The compound which is N-[3-[2,3-Dichloro-4-(2-methylene-1-oxobutyl)phenoxy] acetylthio-2-methyl-propanoyl]-N-cyclopentyl glycine and its pharmaceutically acceptable salts and esters.

5. The compound which is N-[3-(4-chloro-2-[(2-furanylmethyl) amino]-5-sulfamoyl) benzoylthio-2-methylpropanoyl]-N-cyclopentyl glycine t-butyl ester.

6. The compound which is N-[3-(4-chloro-2-[(2-furanylmethyl)amino]-5-sulfamoyl) benzoylthio-2-methylpropanoyl]-N-cyclopentyl glycine and its pharmaceutically acceptable salts and esters.

7. A therapeutic composition comprising, in combination with at least one non-toxic pharmaceutically acceptable extender, an angiotensin converting enzyme inhibiting and diuresis-inducing amount of at least one compound of the formula

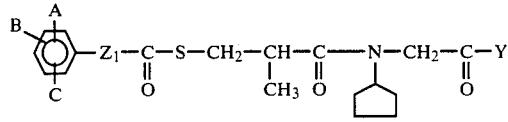

and pharmaceutically acceptable salts thereof; wherein
$Z_1$ is a chemical bond or OCH$_2$—,
A and B are independently hydrogen, halogen or —SO$_1$NH$_2$,
C is hydrogen,

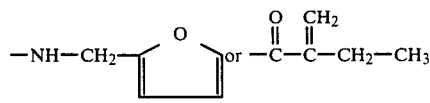

with the proviso that at least one of A, B, or C is other than hydrogen, and
Y is hydroxy or lower alkoxy.

8. A therapeutic composition comprising in combination with at least one non-toxic pharmaceutically acceptable extender, an angiotension converting enzyme inhibiting and diuresis-inducing amount of N-[3[2,3-Dichloro-4-(2-methylene-1-oxobutyl)phenoxy] acetylthio-2-methylpropanoyl]-N-cyclopentyl glycine methyl ester.

9. A therapeutic composition comprising in combination with at least one non-toxic pharmaceutically acceptable extender, an angiotension converting enzyme inhibiting and diuresis-inducing amount of N-[3 [-2,3-Dichloro-4-(2-methylene-1-oxobutyl)phenoxy] acetylthio-2-methylpropanoyl]-N-cyclopentyl glycine t-butyl ester.

10. A therapeutic composition comprising in combination with at least one non-toxic pharmaceutically acceptable extender, an angiotension converting enzyme inhibiting and diuresis-inducing amount of N-[3-[2,3-Dichloro-4-(2-methylene-1-oxobutyl)phenoxy] acetylthio-2-methylpropanoyl]-N-cyclopentyl glycine or its pharmaceutically acceptable salts or esters.

11. A therapeutic composition comprising in combination with at least one non-toxic pharmaceutically acceptable extender, an angiotension converting enzyme inhibiting and diuresis-inducing amount of N-[3-(4-chloro-2-[(2-furanylmethyl)amino]-5-sulfamoyl)-benzoylthio-2methylpropanoyl]-N-cyclopentyl glycine t-butyl ester.

12. A therapeutic composition comprising in combination with at least one non-toxic pharmaceutically acceptable extender, an angiotension converting enzyme inhibiting and diuresis-inducing amount of N-[3-(4-chloro-2-[(2-furanylmethyl)amino]-5-sulfamoyl)-benzoylthio-2-methylpropanoyl]-N-cyclopentyl glycine or its phamaceutically acceptable salts or ester.

13. A method of simultaneously treating angiotension related hypertension and volume overload hypertension which comprises administering to a human host a therapeutically effective amount of at least one compound of the formula

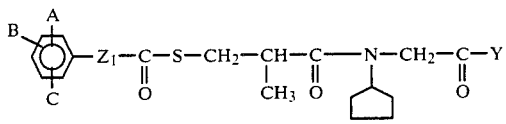

and pharmaceutically acceptable salts thereof; wherein
$Z_1$ is a chemical bond or —OCH$_2$—,
A and B are independently hydrogen, halogen or —SO$_2$NH$_2$,
C is hydrogen,

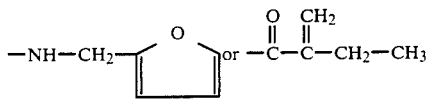

with the proviso that at least one of A, B, or C is other than hydrogen, and
Y is hydroxy or lower alkoxy.

14. A method of simultaneously treating angiotension related hypertension and volume overload hypertension which comprises administering to a human host a therapeutically effective amount of the compound N-[3-[2,3-Dichloro-4-(2-methylene-1-oxobutyl)phenoxy acetylthio-2-methylpropanoyl]-N-cyclopentyl glycine methyl ester.

15. A method of simultaneously treating angiotension related hypertension and volume overload hypertension which comprises administering to a human host a therapeutically effective amount of the compound N-[3-[2,3-Dichloro-4-(2-methylene-1-oxobutyl)phenoxy[ acetylthio-2-methylpropanoyl]-N-cyclopentyl glycine t-butyl ester.

16. A method of simultaneously treating angiotension related hypertension and volume overload hypertension which comprises administering to a human host a therapeutically effective amount of the compound N-[3-[2,3-Dichloro-4-(2-methylene-1-oxobutyl)phenoxy] acetylthio-2-methylpropanoyl]-N-cyclopentyl glycine and its pharmaceutically acceptable salts and esters.

17. A method of simultaneously treating angiotension related hypertension and volume overload hypertension which comprises administering to a human host a therapeutically effective amount of the compound N-[3-(4-chloro-2-[(2-furanylmethyl)amino]-5-sulfamoyl) benzoylthio-2-methylpropanoyl]-N-cyclopentyl glycine t-butyl ester.

18. A method of simultaneously treating angiotension related hypertension and volume overload hypertension which comprises administering to a human host a therapeutically effective amount of the compound N-[3-(4-chloro-2-[(2-furanylmethyl)amino]-5-sulfamoyl) benzoylthio-2-methylpropanoyl]-N-cyclopentyl glycine and its pharmaceutically acceptable salts and esters.

* * * * *